United States Patent [19]

Flanigen et al.

[11] Patent Number: 4,888,167
[45] Date of Patent: Dec. 19, 1989

[54] GERMANIUM-ALUMINUM-PHOSPHORUS-OXIDE MOLECULAR SIEVE COMPOSITIONS

[75] Inventors: Edith M. Flanigen, White Plains; Brent M. T. Lok, New City; Robert L. Patton, Katonah; Stephen T. Wilson, Shrub Oak, all of N.Y.

[73] Assignee: UOP, Des Plaines, Ill.

[21] Appl. No.: 841,753

[22] Filed: Mar. 20, 1986

Related U.S. Application Data

[63] Continuation-in-part of Ser. No. 599,807, Apr. 13, 1984, abandoned.

[51] Int. Cl.$^4$ ............................................. C01B 25/26
[52] U.S. Cl. ..................................... 423/306; 502/208
[58] Field of Search ................ 423/306, 326, 328, 329, 423/330; 502/208

[56] References Cited

U.S. PATENT DOCUMENTS

| | | | |
|---|---|---|---|
| 3,702,886 | 11/1972 | Argauer et al. | 423/328 |
| 3,941,871 | 3/1976 | Dwyer et al. | 423/326 |
| 4,061,724 | 12/1977 | Grose et al. | 423/335 |
| 4,175,114 | 11/1979 | Plank et al. | 423/329 |
| 4,205,052 | 5/1980 | Rollmann et al. | 423/329 |
| 4,208,305 | 6/1980 | Kouwenhoven et al. | 423/328 |
| 4,310,440 | 1/1982 | Wilson et al. | 423/305 |
| 4,323,481 | 4/1982 | Kaduk | 423/329 |
| 4,360,419 | 11/1982 | Miller | 423/328 |
| 4,366,135 | 12/1982 | Le Van Mao et al. | 423/329 |
| 4,372,930 | 2/1983 | Short et al. | 423/326 |
| 4,377,502 | 3/1983 | Klotz | 423/329 |
| 4,390,457 | 6/1983 | Klotz | 423/328 |
| 4,397,825 | 8/1983 | Whittam | 423/329 |
| 4,401,637 | 8/1983 | Marosi et al. | 423/329 |
| 4,420,467 | 12/1983 | Whittam | 423/328 |
| 4,440,871 | 4/1984 | Lok et al. | 502/214 |
| 4,481,173 | 11/1984 | Chu | 423/329 |
| 4,482,531 | 11/1984 | Kuehl | 423/329 |
| 4,483,835 | 11/1984 | Zones | 423/326 |
| 4,500,651 | 2/1985 | Lok et al. | 502/208 |
| 4,508,837 | 4/1985 | Zones | 423/326 |
| 4,510,256 | 4/1985 | Zones | 423/326 |
| 4,511,547 | 4/1985 | Iwayama et al. | 423/329 |
| 4,523,047 | 6/1985 | Chester et al. | 502/71 |
| 4,528,171 | 7/1985 | Casci et al. | 423/326 |
| 4,537,754 | 8/1985 | Casci et al. | 423/326 |
| 4,544,538 | 10/1985 | Zones | 423/326 |
| 4,544,539 | 10/1985 | Wortel | 423/328 |
| 4,554,143 | 11/1985 | Messina et al. | 423/306 |
| 4,567,029 | 1/1986 | Wilson et al. | 423/306 |
| 4,581,211 | 4/1986 | Araya et al. | 423/328 |
| 4,581,212 | 4/1986 | Araya et al. | 423/328 |
| 4,610,854 | 9/1986 | Zones | 423/326 |

FOREIGN PATENT DOCUMENTS

| | | | |
|---|---|---|---|
| 0054364 | 6/1982 | European Pat. Off. | |
| 0055046 | 6/1982 | European Pat. Off. | |
| 0059059 | 6/1982 | European Pat. Off. | |
| 0055529 | 7/1982 | European Pat. Off. | |
| 0147991 | 7/1985 | European Pat. Off. | 423/306 |
| 1527972 | 6/1968 | France | 423/306 |

OTHER PUBLICATIONS

Barrer, R., "Hydrothermal Chemistry of Zeolites", Academic Press, 1982, pp. 251, 282–283.
Chudinova et al, "Preparation of Double Condensed Phosphates of Gallium and Alkali Metals", *Inorg. Mater.*, vol. 15, No. 12, pp. 1710–1713 (1979).
Haggin Chemical & Engineering, Jun. 20, 1983, pp. 36 & 37.

*Primary Examiner*—John Doll
*Assistant Examiner*—R. Bruce Breneman
*Attorney, Agent, or Firm*—Thomas K. McBride; Eugene I. Snyder; Frank S. Molinaro

[57] ABSTRACT

Molecular sieve compositions having three-dimensional microporous framework structures of $GeO_2$, $AlO_2$ and $PO_2$ tetrahedral oxide units are disclosed. These molecular sieves have an empirical chemical composition on an anhydrous basis expressed by the formula:

$$mR: (Ge_xAl_yP_z)O_2$$

wherein "R" represents at least one organic templating agent present in the intracrystalline pore system; "m" represents the molar amount of "R" present per mole of $(Ge_xAl_yP_z)O_2$; and "x", "y" and "z" represent the mole fractions of germanium, aluminum and phosphorus, respectively, present as tetrahedral oxides. Their use as adsorbents, catalysts, etc. is also disclosed.

28 Claims, 3 Drawing Sheets

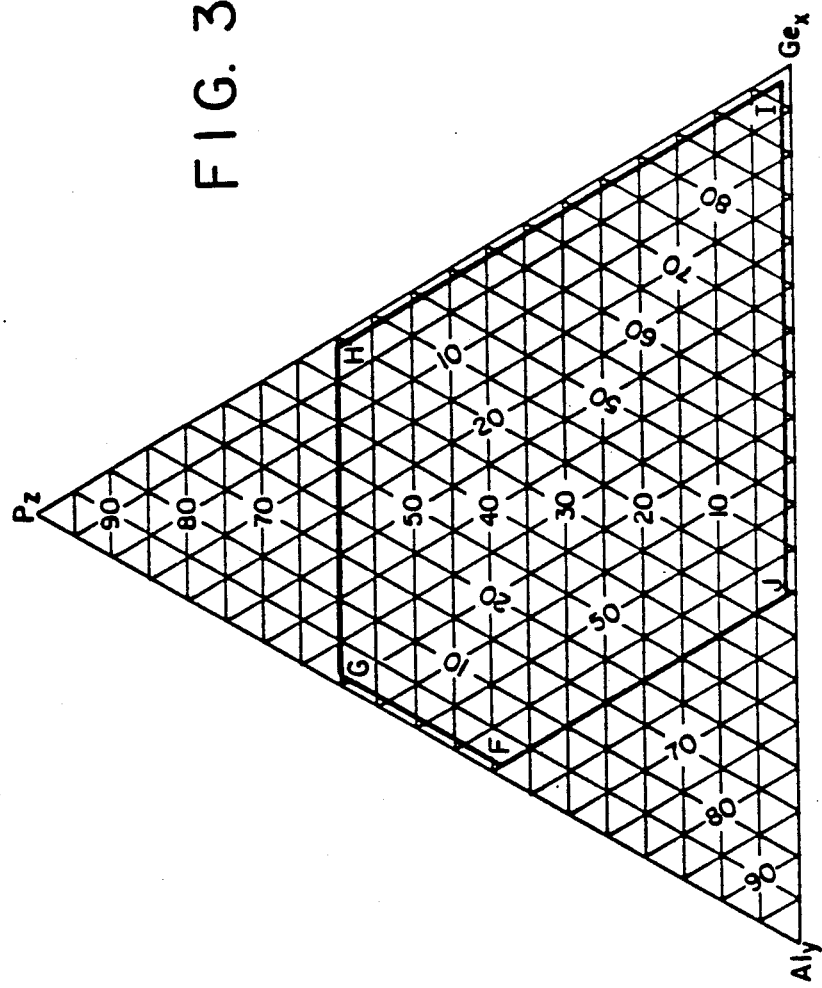

GERMANIUM-ALUMINUM-PHOSPHORUS-OXIDE MOLECULAR SIEVE COMPOSITIONS

This application is a continuation-in-part of our co-pending application Ser. No. 599,807, filed Apr. 13, 1984, now abandoned.

FIELD OF THE INVENTION

The instant invention relates to a novel class of crystalline microporous molecular sieves and to the method of their preparation. The invention relates to novel germanium-aluminum-phosphorus-oxide molecular sieves containing framework tetrahedral oxide units of germanium, aluminum and phosphorus. These compositions may be prepared hydrothermally from gels containing reactive compounds of germanium, aluminum and phosphorus capable of forming framework tetrahedral oxides, and preferably at least one organic templating agent which functions in part to determine the course of the crystallization mechanism and the structure of the crystalline product.

BACKGROUND OF THE INVENTION

Molecular sieves of the crystalline alumino-silicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline alumino-phosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In U.S. Pat. No. 4,440,871 there is described a novel class of silicon-substituted alumino-phosphates which are both microporous and crystalline. The materials have a three dimensional crystal framework of $PO_2^+$, $AlO_2^-$ and $SiO_2$ tetrahedral units and, exclusive of any alkali metal or calcium which may optionally be present, an as-synthesized empirical chemical composition on an anhydrous basis of:

$$mR (Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In U.S. Pat. No. 4,500,651, there is described a novel class of titanium-containing molecular sieves whose chemical composition in the as-synthesized and anhydrous form is represented by the unit empirical formula:

$$mR: (Ti_xAl_yP_z)O_2$$

wherein "R" represents at least one organic templating agent present in the intracrystalline pore system; "m" represents the moles of "R" present per mole of $(Ti_xAl_yP_z)O_2$ and has a value of between zero and about 5.0; and "x", "y" and "z" represent the mole fractions of titanium, aluminum and phosphorus, respectively, present as tetrahedral oxides.

In U.S. Pat. No. 4,567,029, there is described a novel class of crystalline metal alumino-phosphates having three-dimensional microporous framework structures of $MO_2$, $AlO_2$ and $PO_2$ tetrahedral units and having an empirical chemical composition on an anhydrous basis expressed by the formula:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3; "M" represents at least one metal of the group magnesium, manganese, zinc and cobalt; "x", "y", and "z" represent the mole fractions of the metal "M", aluminum and phosphorus, respectively, present as tetrahedral oxides.

In U.S. Pat. No. 4,544,143, there is described a novel class of crystalline ferroaluminophosphates having a three-dimensional microporous framework structure of $Fe_2$, $AlO_2$ and $PO_2$ tetrahedral units and having an empirical chemical composition on an anhydrous basis expressed by the formula:

$$mR:(Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3; and "x", "y" and "z" represent the mole fractions of the iron, aluminum and phosphorus, respectively, present as tetrahedral oxides.

The instant invention relates to new molecular sieve compositions comprising framework tetrahedral units of $GeO_2$, $AlO_2^-$ and $PO_2^+$.

DESCRIPTION OF THE FIGURES

FIG. 3 is a ternary diagram wherein parameters relating to the reaction mixtures employed in the preparation of the compositions of this invention are set forth as mole fractions.

SUMMARY OF THE INVENTION

Figure 1:
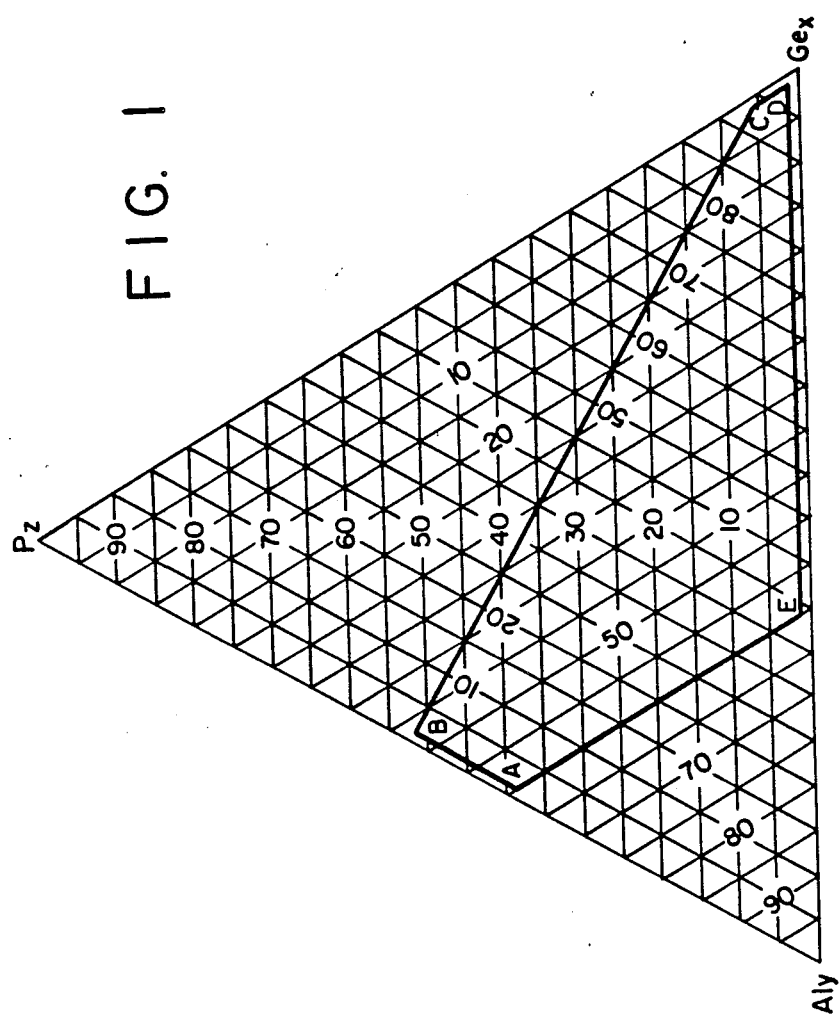
FIG. 1 is a ternary diagram wherein parameters relating to the instant compositions are set forth as mole fractions.

The instant invention relates to a new class of germanium-aluminum-phosphorus-oxide molecular sieves having a crystal framework structure of $GeO_2$, $AlO_2^-$ and $PO_2^+$ tetrahedral oxide units. These new molecular sieves exhibit ion-exchange, adsorption and catalytic properties and, accordingly, find wide use as adsorbents and catalysts. The members of this novel class of compositions have crystal framework structures of $GeO_2$, $AlO_2^-$ and $PO_2^+$ tetrahedral units and have an empirical chemical composition on an anhydrous basis expressed by the formula:

$$mR\ (Ge_xAl_yP_z)O_2$$

wherein "R" represents at least one organic templating agent present in the intracrystalline pore system; "m" represents the molar amount of "R" present per mole of $(Ge_xAl_yP_z)O_2$ and has a value of zero to about 0.3; and "x", "y" and "z" represent the mole fractions of germanium, aluminum and phosphorus, respectively, present as tetrahedral oxides. These molecular sieve compositions comprise crystalline molecular sieves having a three-dimensional microporous framework structure of $GeO_2$, $AlO_2^-$ and $PO_2^+$ tetrahedral units.

The molecular sieves of the instant invention will be generally referred to by the acronym "GeAPO" to designate the framework of $GeO_2$, $AlO_2^-$ and $PO_2^+$ tetrahedral units. Actual class members will be identified by denominating the various structural species which make up the GeAPO class by assigning a number and, accordingly, are identified as "GeAPO-i" wherein "i" is an integer. The given species designation is not intended to denote a similarity in structure to any other species denominated by a numbering system.

DETAILED DESCRIPTION OF THE INVENTION

The instant invention relates to a new class of germanium-aluminum-phosphorus molecular sieves comprising a crystal framework structure of $GeO_2$, $AlO_2^-$ and $PO_2^+$ tetrahedral oxide units. These new molecular sieves exhibit ion-exchange, adsorption and catalytic properties and, accordingly, find wide use as adsorbents and catalysts.

The GeAPO molecular sieves have three-dimensional microporous framework structures of $GeO_2$, $AlO_2^-$, and $PO_2^+$ tetrahedral oxide units having an empirical chemical composition on an anhydrous basis expressed by the formula:

$$mR\ (Ge_xAl_yP_z)O_2$$

wherein "R" represents at least one organic templating agent present in the intracrystalline pore system; "m" represents the molar amount of "R" present per mole of $(Ge_xAl_yP_z)O_2$ and has a value of zero to about 0.3, but is preferably not greater than about 0.2; and "x", "y" and "z" represent the mole fractions of germanium, aluminum and phosphorus, respectively, present as tetrahedral oxides. The mole fractions "x", "y", and "z" are generally defined as being within the pentagonal compositional area defined by points A, B, C, D, and E of the ternary diagram of FIG. 1. Points A, B, C, D, and E of FIG. 1 have the following values for "x", "y", and "z":

| Point | Mole Fraction | | |
|---|---|---|---|
| | x | y | z |
| A | 0.01 | 0.60 | 0.39 |
| B | 0.01 | 0.47 | 0.52 |
| C | 0.94 | 0.01 | 0.05 |
| D | 0.98 | 0.01 | 0.01 |
| E | 0.39 | 0.60 | 0.01 |

Figure 2:
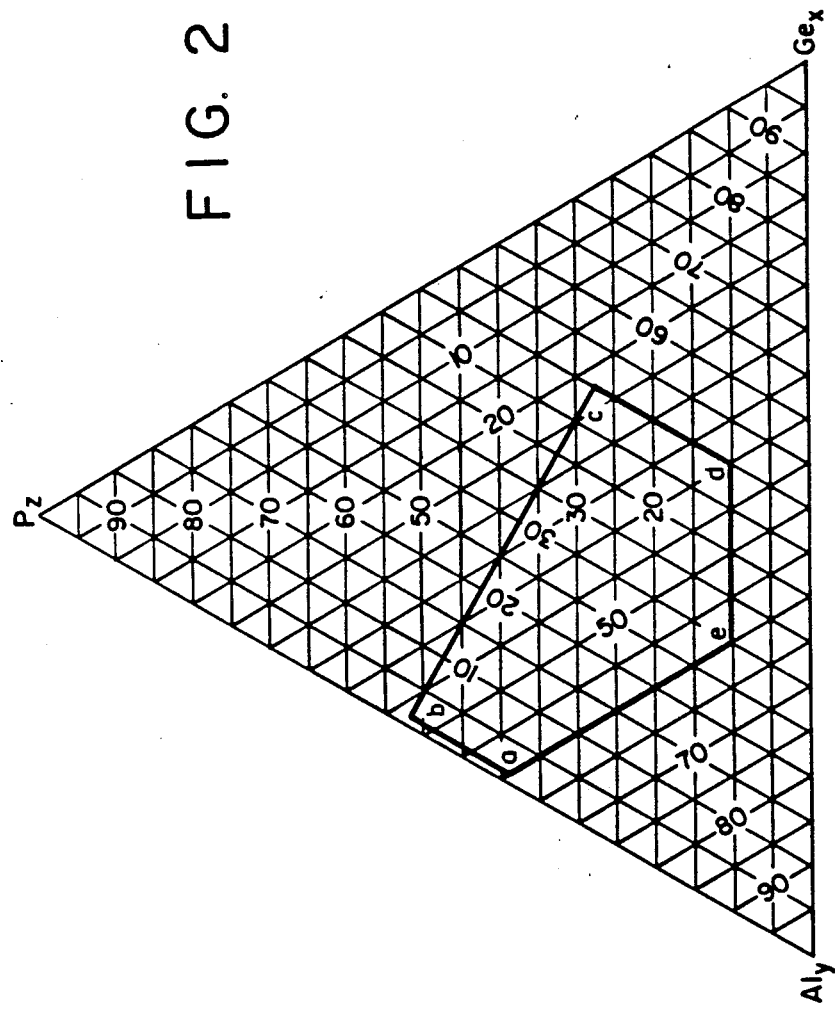
FIG. 2 is a ternary diagram wherein parameters relating to preferred compositions are set forth as mole fractions.

In a preferred subclass of the GeAPO molecular sieves the values of "x", "y" and "z" in the above formula are within the pentagonal compositional area defined by the points a, b, c, d and e of the ternary diagram which is FIG. 2 of the drawings, said points a, b, c, d and e representing the following values for "x", "y" and "z":

| Point | Mole Fraction | | |
|---|---|---|---|
| | x | y | z |
| a | 0.01 | 0.60 | 0.39 |
| b | 0.01 | 0.47 | 0.52 |
| c | 0.50 | 0.225 | 0.275 |
| d | 0.50 | 0.40 | 0.10 |
| e | 0.30 | 0.60 | 0.10 |

An especially preferred subclass of the GeAPO molecular sieves are those in which the value of "x" is not greater than about 0.13.

The GeAPOs of this invention are useful as adsorbents, catalysts, ion-exchangers, and the like in much the same fashion as aluminosilicates have been employed heretofore, although their chemical and physical properties are not necessarily similar to those observed for aluminosilicates.

GeAPO compositions are generally synthesized by hydrothermal crystallization from a reaction mixture containing reactive sources of germanium, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure, at a temperature between 50° and 250° C., and preferably between 100° C. and 200° C. until crystals of the GeAPO product are obtained, usually a period of from several hours to several weeks. Typical crystallization times are from about 2 hours to about 30 days, with from about 2 hours to about 20 days, and preferably about 1 to about 10 days, generally being employed to obtain crystals of the GeAPO products. The product is recovered by any convenient method such as centrifugation or filtration.

In synthesizing the GeAPO compositions of the instant invention, it is preferred to employ a reaction mixture composition expressed in terms of the molar ratios as follows:

$$aR: (Ge_wAl_uP_v)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not greater than about 0.6; "b" has a value of from zero (0) to about 500, preferably between about 2 and about 300, most preferably between about 10 and about 60; and "w", "u" and "v" represent the mole fractions of germanium, aluminum and phosphorus, respectively, and each has a value of at least 0.01. The mole fractions "w", "u" and "v" in the reaction mixture are preferably within pentagonal compositional area defined by points F, G, H, I, and J which is shown in FIG. 3 of the drawings, where points F, G, H, I, and J have the following values for "w", "u" and "v":

| Point | Mole Fraction | | |
|---|---|---|---|
| | w | u | v |
| F | 0.01 | 0.60 | 0.39 |
| G | 0.01 | 0.39 | 0.60 |
| H | 0.39 | 0.01 | 0.60 |
| I | 0.98 | 0.01 | 0.01 |
| J | 0.39 | 0.60 | 0.01 |

Especially preferred reaction mixtures are those containing from about 0.2 to 0.4 moles of $GeO_2$ and from 0.75 to 1.25 moles of $Al_2O_3$ for each mole of $P_2O_5$.

In the foregoing expression of the reaction composition, the reactants are normalized with respect to the total of w+u+v=1.00 mole, whereas in the examples the reaction mixtures are expressed in terms of the molar oxide ratios and may be normalized to 1.00 mole of $P_2O_5$ and/or 1.00 mole of $Al_2O_3$. These latter forms are readily converted to the former form by routine calculation by dividing the total number of moles of germanium, aluminum and phosphorus into the moles of each of germanium, aluminum and phosphorus. The moles of template and water are similarly normalized.

In forming the reaction mixture from which the instant molecular sieves are formed the organic templating agent can be any of those heretofore proposed for used in the synthesis of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium compounds and quaternary ammonium compounds, the latter two being represented generally by the formula $R_4X^+$ wherein "X" is nitrogen or phosphorus and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents can either produce mixtures of the desired GeAPOs or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; tetrapentylammonium ion; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo (2,2,2,) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N,-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. to every templating agent will direct the formation of every species of GeAPO, i.e., a single templating agent can, with proper manipulation of the reaction conditions, direct the formation of several GeAPO compositions, and a given GeAPO composition can be produced using several different templating agents.

The reactive phosphorus source is preferably phosphoric acid, but organic phosphates such as triethyl phosphate may be satisfactory, and so also may crystalline or amorphous aluminophosphates such as the $AlPO_4$ composition of U.S. Pat. No. 4,310,440. Organophosphorus compounds, such as tetrabutylphosphonium bromide, do not apparently serve as reactive sources of phosphorus, but these compounds may function as templating agents. Conventional phosphorus salts such as sodium metaphosphate, may be used, at least in part, as the phosphorus source, but are not preferred.

The preferred aluminum source is either an aluminum alkoxide, such as aluminum isopropoxide, aluminum sec-butoxide or pseudoboehmite. Aluminum chlorhydrol ($Al_2Cl(OH)_5.2H_2O$) may also be employed. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The reactive source of germanium can be introduced into the reaction system in any form which permits the formation in situ of a reactive form of germanium, i.e., reactive to form the framework tetrahedral oxide unit of germanium. Compounds of germanium which may be employed include oxides, alkoxides, hydroxides, chlorides, bromides, iodides, nitrates, sulfates, carboxylates, organo-germanium compounds and the like. Especially preferred sources of germanium are germanium tetrachloride, germanium ethoxide and germanium dioxide.

As illustrated in some of the Examples below, in some cases it may be advantageous, when synthesizing the GeAPO compositions of the present invention, to first combine germanium and aluminium sources to form a mixed germanium aluminum compound, typically a mixed germanium aluminum oxide, and thereafter to combine this mixed germanium aluminum compound with a source of phosphorus to produce the final GeAPO composition.

While not essential to the synthesis of GeAPO compositions, stirring or other moderate agitation of the reaction mixture and/or seeding the reaction mixture with seed crystals of either the GeAPO species to be produced or a topologically similar aluminophosphate, aluminosilicate or molecular sieve composition, facilitates the crystallization procedure.

After crystallization the GeAPO product may be isolated and advantageously washed with water and dried in air. The as-synthesized GeAPO generally contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular GeAPO species. As a general rule the templating agent, and hence the occluded organic species, is too large to move freely through the pore system of the GeAPO product and must be removed by calcining the GeAPO at temperatures of 200° C. to 700° C., preferably about 350° C. to about 600° C., to thermally degrade the organic species. In a few instances the pores of the GeAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the GeAPO phase wherein the organic moiety occupying the intracrystalline pore system as a result of the hydrothermal crystallzation process has been reduced by post-synthesis treatment such that the value of "m" in the composition formula

$$mR:Ge_xAl_yP_z)O_2$$

has a value of less than 0.02. The other symbols of the formula are as defined hereinabove. In those preparations in which an alkoxide is employed as the source of germanium, aluminum or phosphorus, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized GeAPO material.

Since the present GeAPO compositions are formed from $GeO_2$, $AlO_2$ and $PO_2^+$ tetrahedral units which, respectively, have a net charge of 0, $-1$ and $+1$, the matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^+$ tetrahedron or a simple cation such as an alkali metal cation, a proton ($H^+$), a cation of germanium present in the reaction mixture, or an organic cation derived from the templating agent. It has also been postulated that non-adjacent $AlO_2^-$ and $PO_2^+$ tetrahedral pairs can be balanced by $Na^+$ and $OH^-$ respectively [Flanigen and Grose, Molecular Sieve Zeolites-I, ACS, Washington, DC (1971)].

The GeAPO compositions of the present invention may exhibit cation-exchange capacity when analyzed using ion-exchange techniques heretofore employed with zeolitic aluminosilicates and have pore diameters which are inherent in the lattice structure of each species and which are at least about 3Å in diameter. Ion exchange of GeAPO compositions would ordinarily be possible only after any organic moiety derived from the template, present as a result of synthesis, has been removed from the pore system. Dehydration to remove water present in the as-synthesized GeAPO compositions can usually be accomplished, to some degree at least, in the usual manner without removal of the organic moiety, but the absence of the organic species greatly facilitates adsorption and desorption procedures. The GeAPO materials have various degrees of hydrothermal and thermal stability, some being quite remarkable in this regard, and function well as molecular sieve adsorbents and hydrocarbon conversion catalysts or catalyst bases.

In preparing the GeAPO composition it is preferred to use a stainless steel reaction vessel lined with an inert plastic material, e.g., polytetrafluoroethylene, to avoid contamination of the reaction mixture. In general, the final reaction mixture from which each GeAPO composition is crystallized is prepared by forming mixtures of less than all of the reagents and thereafter incorporating into these mixtures additional reagents either singly or in the form of other intermediate mixtures of two or more reagents. In some instances the reagents admixed retain their identity in the intermediate mixture and in other cases some or all of the reagents are involved in chemical reactions to produce new reagents. The term "mixture" is applied in both cases. Further, it is preferred that the intermediate mixtures as well as the final reaction mixtures be stirred until substantially homogeneous.

X-ray patterns of reaction products are obtained by X-ray analysis using standard X-ray powder diffraction techniques. The radiation source is a high-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of diffraction peaks expressed as $2\theta$ where $\theta$ is the Bragg angle as observed on the strip chart. Intensities are determined from the heights of diffraction peaks after subtracting background, "$I_o$" being the intensity of the strongest line or peak, and "I" being the intensity of each of the other peaks. Alternatively, the X-ray patterns may be obtained by use of copper K-alpha radiation with Siemens K-805 X-ray sources with computer based techniques using Seimens D-500 X-ray powder diffractometers, available from Siemens Corporation, Cherry Hill, N.J.

As will be understood by those skilled in the art the determination of the parameter 2 theta is subject to both human and mechanical error, which in combination, can impose an uncertainty of about ±0.4 reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak, respectively.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their X-ray powder diffraction patterns and as such may have one of the X-ray patterns set forth in the following Tables A through V, wherein said X-ray patterns are for the as-synthesized form unless otherwise noted. In most cases, the pattern of the corresponding calcined form will also fall within the relevant Table. However, in some cases the removal of the occluded templating agent which occurs during calcination will be accompanied by sufficient relaxation of the lattice to shift some of the lines slightly outside the ranges specified in the relevant Table. In a small number of cases, calcination appears to cause more substantial distortions in the crystal lattice, and hence more significant changes in the X-ray powder diffraction pattern.

TABLE A

| 2θ | (GeAPO-5) d(Å) | Relative Intensity |
|---|---|---|
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

TABLE B

| 2θ | (GeAPO-11) d(Å) | Relative Intensity |
|---|---|---|
| 9.3–9.65 | 9.51–9.17 | m–s |
| 20.2–20.6 | 4.40–4.31 | m–s |
| 20.9–21.3 | 4.25–4.17 | s–vs |
| 22.0–22.5 | 4.04–3.95 | m–s |
| 22.5–22.9 | 3.95–3.92 | m–s |
| 23.0–23.4 | 3.87–3.80 | m–vs |

TABLE C

| 2θ | (GeAPO-14) d(Å) | Relative Intensity |
|---|---|---|
| 8.6–8.9 | 10.39–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE D

| 2θ | (GeAPO-16) d(Å) | Relative Intensity |
|---|---|---|
| 11.3–11.6 | 7.83–7.63 | m–vs |
| 18.7–18.9 | 4.75–4.70 | w–s |

TABLE D-continued

| 2θ | (GeAPO-16) d(Å) | Relative Intensity |
|---|---|---|
| 21.9–22.3 | 4.06–3.99 | m–vs |
| 26.5–27.0 | 3.363–3.302 | w–m |
| 29.7–30.05 | 3.008–2.974 | w–m |

TABLE E

| 2θ | (GeAPO-17) d(Å) | Relative Intensity |
|---|---|---|
| 7.7–7.75 | 11.5–11.4 | vs |
| 13.4 | 6.61 | s–vs |
| 15.5–15.55 | 5.75–5.70 | s |
| 20.5–20.6 | 4.33–4.31 | vs |
| 31.8–32.00 | 2.812–2.797 | w–s |

TABLE F

| 2θ | (GeAPO-18) d(Å) | Relative Intensity |
|---|---|---|
| 9.6–9.7 | 9.21–9.11 | vs |
| 15.5–15.6 | 5.72–5.70 | w–m |
| 16.9–17.1 | 5.25–5.19 | m |
| 20.15–20.25 | 4.41–4.39 | m |
| 20.95–21.05 | 4.24–4.22 | w–m |
| 31.8–32.6 | 2.814–2.75 | m |

TABLE G

| 2θ | (GeAPO-20) d(Å) | Relative Intensity |
|---|---|---|
| 13.7–14.25 | 6.46–6.22 | m–vs |
| 19.55–20.0 | 4.54–4.44 | w–s |
| 24.05–24.5 | 3.70–3.63 | m–vs |
| 34.3–35.0 | 2.614–2.564 | vw–w |
| 42.5–43.0 | 2.127–2.103 | vw–w |

TABLE H

| 2θ | (GeAPO-31) d(Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

TABLE J

| 2θ | *(GeAPO-33) d(Å) | Relative Intensity |
|---|---|---|
| 9.25–9.55 | 9.56–9.26 | w–m |
| 12.5–12.9 | 7.08–6.86 | vs |
| 15.3 | 5.79 | w |
| 26.05–26.35 | 3.42–3.38 | w–m |
| 27.3–27.6 | 3.27–3.23 | vs |
| 40.0 | 2.25 | w |

*as-synthesized form

TABLE K

| 2θ | *(GeAPO-33) d(Å) | Relative Intensity |
|---|---|---|
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L

| | (GeAPO-34) | |
|---|---|---|
| 2θ | d(Å) | Relative Intensity |
| 9.4–9.65 | 9.41–9.17 | s–vs |
| 15.9–16.2 | 5.57–5.47 | vw–m |
| 17.85–18.4 | 4.97–4.82 | w–s |
| 20.3–20.9 | 4.37–4.25 | m–vs |
| 24.95–25.4 | 3.57–3.51 | vw–s |
| 30.3–30.8 | 2.95–2.90 | w–s |

TABLE M

| | (GeAPO-35) | |
|---|---|---|
| 2θ | d(Å) | Relative Intensity |
| 10.8–11.1 | 8.19–7.97 | m |
| 17.2–17.4 | 5.16–5.10 | s–vs |
| 21.0–21.25 | 4.23–4.18 | m–s |
| 21.8–22.0 | 4.08–4.04 | vs |
| 31.8–32.2 | 2.814–2.788 | m |

TABLE N

| | (GeAPO-36) | |
|---|---|---|
| 2θ | d(Å) | Relative Intensity |
| 7.7–7.9 | 11.5–11.2 | vs |
| 16.2–16.6 | 5.47–5.34 | w–m |
| 18.9–19.3 | 4.70–4.60 | m–s |
| 20.6–20.8 | 4.31–4.27 | w–s |
| 21.8–22.0 | 4.08–4.04 | m |
| 22.2–22.5 | 4.00–3.95 | w–m |

TABLE O

| | (GeAPO-37) | |
|---|---|---|
| 2θ | d(Å) | Relative Intensity |
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

| | (GeAPO-39) | |
|---|---|---|
| 2θ | d(Å) | Relative Intensity |
| 9.4–9.6 | 9.41–9.21 | w–m |
| 13.3–13.6 | 6.66–6.51 | m–vs |
| 18.0–18.4 | 4.93–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE Q

| | (GeAPO-40) | |
|---|---|---|
| 2θ | d(Å) | Relative Intensity |
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

| | (GeAPO-41) | |
|---|---|---|
| 2θ | d(Å) | Relative Intensity |
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.440 | w–m |

TABLE S

| | (GeAPO-42) | |
|---|---|---|
| 2θ | d(Å) | Relative Intensity |
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |
| 30.05–30.25 | 2.974–2.955 | m–s |

TABLE T

| | (GeAPO-44) | |
|---|---|---|
| 2θ | d(Å) | Relative Intensity |
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

TABLE U

| | (GeAPO-46) | |
|---|---|---|
| 2θ | d(Å) | Relative Intensity |
| 7.2–8.1 | 12.3–10.9 | vs |
| 21.2–21.8 | 4.19–4.08 | w–m |
| 22.5–23.0 | 3.95–3.87 | vw–m |
| 26.6–27.2 | 3.351–3.278 | vw–w |
| 28.5–29.0 | 3.132–3.079 | vw–w |

TABLE V

| | (GeAPO-47) | |
|---|---|---|
| 2θ | d(Å) | Relative Intensity |
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w |

The following examples are provided to further illustrate the invention and are not intended to be limiting thereof:

EXAMPLE 1

(Preparation of A $Al_2O_3/GeO_2$ Precursor)

100 grams of 99.9% pure germanium tetrachloride ($GeCl_4$) were mixed with 676 grams of aluminum chlorhydrol ($Al_2Cl(OH)_5 \cdot 2.0\ H_2O$). The composition of this mixture, expressed in terms of the molar oxide ratios of its components, was:

$$0.3\ GeO_2 : 1.0\ Al_2O_3$$

The resultant mixture was reduced in volume using a rotary evaporator until a thick gel was obtained, this gel was diluted with water and a solid mixture of oxides precipitated by slow addition of concentrated ammonium hydroxide until the pH reached approximately 8.0.

In order to remove all traces of the liquid phase, the oxide mixture was washed twice by centrifugation, filtered and washed free of chloride ion with a dilute ammonium hydroxide solution having a pH of approximately 8. The solid oxide mixture thus produced was dried at room temperature for several hours and finally dried at 100° C.

A sample of this solid oxide mixture was analyzed and the following chemical analysis obtained:

| Component | Weight Percent |
|---|---|
| $Al_2O_3$ | 51.3 |
| $GeO_2$ | 15.4 |
| Cl | 3.3 |
| LOI* | 32.0 |

*LOI indicates loss on ignition.

The above chemical analysis corresponds to a product composition, on a chloride-free basis, in molar oxide ratios of:

0.29 $GeO_2$:1.0 $Al_2O_3$:3.5 $H_2O$

A portion of the solid oxide mixture thus produced was calcined at 350° C. for three hours. A sample of this solid calcined product was analyzed and the following chemical analysis obtained:

| Components | Weight Percent |
|---|---|
| $GeO_2$ | 17.9 |
| $Al_2O_3$ | 60.0 |
| Cl | 2.8 |
| LOI* | 20.5 |

*LOI indicates loss on ignition.

The above chemical analysis corresponds to a product composition, on a chloride-free basis, in molar oxide ratios of:

0.29 $GeO_2$:1.0 $Al_2O_3$:1.9 $H_2O$

EXAMPLE 2

(Preparation of $Al_2O_3/GeO_2$ Precursor)

(a) To prepare an $Al_2O_3/GeO_2$ precursor, 49.3 grams of aluminum tri-sec-butoxide ($Al(OC_4H_9)_3$) were mixed with 25.3 grams of germanium ethoxide ($Ge(OC_2H_5)_4$). The composition of the resultant mixture, expressed in terms of the molar oxide ratios of the components thereof, was:

1.0 $GeO_2$:1.0 $Al_2O_3$

To the resultant mixture were added 18.0 grams of water with continuous mixing. Severe gelation of the mix occurred, whereafter 40.0 grams of water were added and mixed in. The resultant slurry was dried at 100° C. for several hours to remove the alcohol produced by hydrolysis of the alkoxides, then an additional 70.4 grams of water were added to the dried solids and the resultant slurry dried at 100° C. for several days.

A sample of the resultant solid oxide mixture was analyzed and the following chemical analysis obtained:

| Component | Weight Percent |
|---|---|
| $GeO_2$ | 36.0 |
| $Al_2O_3$ | 34.4 |
| LOI* | 28.8 |

*LOI indicates loss on ignition.

The above chemical analysis corresponds to a product composition in molar oxide ratios of:

1.02 $GeO_2$:1.00 $Al_2O_3$:4.74 $H_2O$.

EXAMPLE 3

(Preparation of GeAPO-5)

(a) To prepare GeAPO-5, a solution was formed by combining 23.1 grams of 85 wt. percent orthophosphoric acid ($H_3PO_4$) with 33.7 grams of water, and adding to the resultant solution 16.1 grams of the dried uncalcined oxide mixture prepared in Example 1 above. To the resultant mixture were added 36.8 grams of 40 wt. percent aqueous tetraethylammonium hydroxide (TEAOH), and the resultant mixture was stirred until it was homogeneous. The composition of the final reaction mixture thus produced, expressed in terms of the molar oxide ratios of the components of the reaction mixture was:

1.0 TEAOH:0.30 $GeO_2$:1.0 $Al_2O_3$:1.0 $P_2O_5$:30.0 $H_2O$.

This final reaction mixture was digested by sealing it in a stainless steel pressure vessel lined with polytetrafluoroethylene and heating it in an oven at 200° C. under autogenous pressure for 72 hours. The solid reaction product (which was determined by the analyses described below to be GeAPO-5) was recovered by centrifugation, washed and dried in air at ambient temperature, then at 100° C. overnight. A sample of the solid reaction product was analyzed and the following chemical analysis obtained:

| Component | Weight Percent |
|---|---|
| Carbon | 6.3 |
| Nitrogen | 0.92 |
| $GeO_2$ | 2.7 |
| $Al_2O_3$ | 35.9 |
| $P_2O_5$ | 50.3 |
| LOI* | 12.9 |

*LOI indicates loss on ignition.

The above chemical analysis corresponds to a product composition, on an anhydrous basis, in molar oxide ratios of:

0.19 TEAOH:0.07 $GeO_2$:1.0 $Al_2O_3$:1.01 $P_2O_5$ and thus to an empirical formula of:

0.05 TEAOH:$(Ge_{0.02}Al_{0.49}P_{0.49})O_2$ so that the product contained germanium, aluminum and phosphorus in amounts within the pentagonal compositional area defined by points A, B, C, D and E of FIG. 1.

Scanning electron microscopy of the product showed numerous crystals with the morphology expected for GeAPO-5. Microprobe analysis of clean crystals having this morphology indicated a composition of:

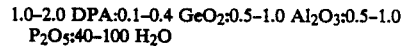

thus again confirming that the product contained germanium, aluminum and phosphorus in amounts within the pentagonal compositional area defined by points A, B, C, D and E of FIG. 1.

The X-ray powder diffraction pattern of the product, as synthesized, was characterized by the data in the following Table AA (Hereinafter, Tables designated AA, AB etc. are tables of X-ray data which include all the peaks mentioned in Table A above and similarly for tables designated EA, EB etc.):

TABLE AA (GeAPO-5)

| $2\theta$ | d(Å) | Relative Intensity $100 \times I/I_o$ |
|---|---|---|
| 7.5 | 11.81 | 100.0 |
| 13.0 | 6.82 | 8.1 |
| 15.0 | 5.91 | 18.7 |
| 19.9 | 4.47 | 38.0 |
| 21.1 | 4.21 | 29.9 |
| 22.5 | 3.95 | 50.2 |
| 26.1 | 3.50 | 15.2 |
| 29.2 | 3.06 | 8.4 |
| 30.2 | 2.96 | 10.1 |
| 34.8 | 2.58 | 7.7 |
| 37.9 | 2.38 | 6.4 |

Other specimens of GeAPO-5 prepared in a similar manner had very similar X-ray diffraction powder patterns. The following general Table AB summarizes the X-ray powder diffraction lines which were obtained from the various specimens of GeAPO-5. The least intense lines were not obtained from every specimen.

TABLE AB (GeAPO-5)

| $2\theta$ | d(Å) | Relative Intensity $100 \times I/I_o$ |
|---|---|---|
| 7.4–7.5 | 11.79–11.88 | 100.0 |
| 12.9–13.0 | 6.81–6.84 | 7.3–8.1 |
| 15.0 | 5.90–5.92 | 18.5–20.7 |
| 19.8–19.9 | 4.46–4.47 | 38.0–49.1 |
| 20.9–21.1 | 4.21–4.26 | 28.7–29.9 |
| 22.5 | 3.95–3.96 | 50.2–59.0 |
| 26.1 | 3.41–3.50 | 15.2–22.6 |
| 29.0–29.2 | 3.06–3.08 | 8.4–6.7 |
| 34.8 | 2.58 | 7.7–11.7 |
| 37.6–37.9 | 2.38–2.39 | 5.8–6.6 |

(b) A sample of the product produced in part (a) was utilized in adsorption capacity studies using a standard McBain-Bakr gravimetric adsorption apparatus. Before being used in the adsorption tests, the sample was calcined in air at 600° C. for 3 hours. The calcined sample was activated by heating to 350° C. for sixteen hours in vacuum, and this activation was repeated before each new adsorbate. The following data were generated in the adsorption studies:

| Adsorbate | Kinetic Diameter (Å) | Pressure (Torr) | Temp. ° C. | Wt. % Adsorbed |
|---|---|---|---|---|
| $O_2$ | 3.46 | 100 | −183 | 14.0 |
| Neopentane | 6.2 | 700 | 23 | 6.8 |
| n-Hexane | 4.3 | 45 | 22 | 6.9 |
| n-Butane | 4.3 | 700 | 22 | 6.7 |
| iso-Butane | 5.0 | 700 | 22 | 5.7 |
| $H_2O$ | 2.65 | 4.6 | 22 | 4.7 |

From the above data, the pore size of the calcined product was determined to be greater than about 6.2 Å, as shown by the adsorption of neopentane (kinetic diameter of 6.2 Å).

EXAMPLE 4

(Preparation of GeAPO-11)

(a) GeAPO-11 is prepared from a reaction mixture having a composition, expressed in terms of the molar oxide ratios of the components of the reaction mixture, of:

1.0–2.0 DPA:0.1–0.4 $GeO_2$:0.5–1.0 $Al_2O_3$:0.5–1.0 $P_2O_5$:40–100 $H_2O$ where "DPA" denotes di-n-propylamine.

The reaction mixture is digested by placing the reaction mixture in a sealed stainless steel pressure vessel and heating it at an effective temperature and for an effective time until crystals of the GeAPO-11 product are obtained. Solids are then recovered by filtration, washed with water and dried in air at room temperature.

The GeAPO-11 product's chemical analysis shows the GeAPO-11 product contains germanium, aluminum and phosphorus in amounts within the pentagonal compositional area defined by points A, B, C, D and E of FIG. 1.

The X-ray powder diffraction pattern of a GeAPO-11 product is characterized by the following data:

| $2\theta$ | d(Å) | Relative Intensity |
|---|---|---|
| 9.3–9.65 | 9.51–9.17 | m–s |
| 20.3–20.6 | 4.40–4.31 | m–s |
| 20.9–21.3 | 4.25–4.17 | s–vs |
| 22.0–22.5 | 4.04–3.95 | m–s |
| 22.5–22.9 | 3.95–3.92 | m–s |
| 23.0–23.4 | 3.87–3.80 | m–vs |

(b) The X-ray powder diffraction pattern for a calcined GeAPO-11 is also characterized by the X-ray pattern of part (a).

(c) When the GeAPO-11 of part (b) is utilized in adsorption capacity studies using a standard McBain-Bakr gravimetric adsorption apparatus the measurements are made on a sample after activation at 350° C. in vacuum. The following data are used in the adsorption studies:

| Adsorbate | Kinetic Diameter (Å) | Pressure (Torr) | Temp. ° C. | Wt. % Adsorbed |
|---|---|---|---|---|
| $O_2$ | 3.46 | 100 | −183 | 5 |
| $O_2$ | 3.46 | 750 | 24 | 6 |
| Cyclohexane | 6.0 | 90 | 24 | 4 |
| $H_2O$ | 2.65 | 4.3 | 24 | 6 |
| $H_2O$ | 2.65 | 20 | 24 | 8 |

*typical amount adsorbed

EXAMPLE 5

(Preparation of GeAPO-17)

(a) To prepare GeAPO-17, a solution was formed by combining 23.1 grams of 85 wt. percent orthophosphoric acid ($H_3PO_4$) with 42.5 grams of water. The resultant solution was mixed with 16.1 grams of the solid, uncalcined product produced in Example 1 above. 9.9 Grams of cyclohexylamine ($C_6H_{13}N$) were then added slowly and the resultant mixture was stirred until it was homogeneous. The composition of the final reaction mixture thus produced, expressed in terms of the molar oxide ratios of the components of the reaction mixture, was:

1.23 ($C_6H_{13}N$):0.29 $GeO_2$:1.00 $Al_2O_3$:1.24 $P_2O_5$:30.0 $H_2O$

This final reaction mixture was digested by sealing it in a stainless steel pressure vessel lined with polytetrafluoroethylene and heating it in an oven at 200° C. under autogenous pressure for 72 hours. The solid reaction product (which was determined by the analyses described below to be principally GeAPO-17) was recovered by centrifugation, and dried in air at ambient temperature and then at 100° C. overnight. A sample of this solid reaction product was analyzed and the following chemical analysis obtained:

| Component | Weight Percent |
|---|---|
| Carbon | 9.3 |
| Nitrogen | 1.7 |
| $GeO_2$ | 6.1 |
| $Al_2O_3$ | 31.9 |
| $P_2O_5$ | 43.7 |
| LOI* | 16.8 |

*LOI indicates loss on ignition.

The above chemical analysis corresponds to a product composition, on an anhydrous basis, in molar oxide ratios of:

0.41 ($C_6H_{13}N$):0.19 $GeO_2$:1.00 $Al_2O_3$:0.98 $P_2O_5$ or an empirical formula, on an anhydrous basis, of:

0.10 ($C_6H_{13}N$):($Ge_{0.04}$ $Al_{0.48}$ $P_{0.47}$)$O_2$ so that the product contained germanium, aluminum and phosphorus in amounts within the pentagonal compositional area defined by points A, B, C, D and E of FIG. 1.

Scanning electron microscopy of the solid reaction product showed numerous crystals with the morphology expected for GeAPO-17. Microprobe analysis of a clean crystal having this morphology indicated the following composition:

$Ge_{0.04}Al_{0.48}P_{0.48}$ again confirming that the product contained germanium, aluminum and phosphorus in amounts within the pentagonal compositional area defined by A, B, C, D and E of FIG. 1.

The X-ray powder diffraction of the product, as synthesized, was characterized by the data in the following Table EA:

TABLE EA
(GeAPO-17)

| $2\theta$ | d(Å) | Relative Intensity 100 × I/I$_o$ |
|---|---|---|
| 7.7 | 11.42 | 35.8 |
| 9.8 | 9.10 | 13.6 |
| 13.4 | 6.608 | 19.2 |
| 14.6 | 6.050 | 5.5 |
| 15.5 | 5.727 | 10.5 |
| 20.5 | 4.332 | 22.4 |
| 23.3 | 3.822 | 6.0 |

TABLE EA-continued
(GeAPO-17)

| $2\theta$ | d(Å) | Relative Intensity 100 × I/I$_o$ |
|---|---|---|
| 23.8 | 3.733 | 4.5 |
| 26.9 | 3.312 | 7.0 |
| 31.2 | 2.866 | 7.2 |
| 31.8 | 2.814 | 7.7 |
| 49.7 | 1.835 | 4.5 |

(b) A sample of the product produced in part (a) was utilized in adsorption capacity studies using a standard McBain-Bakr gravimetric adsorption apparatus. Before being used in the adsorption tests, the sample was calcined in air at 600° C. for 3 hours. The calcined sample was activated by heating to 350° C. for 16 hours in vacuum, and this activation was repeated before each new adsorbate. The following data were generated in the adsorption studies:

| Adsorbate | Kinetic Diameter (Å) | Pressure (Torr) | Temp. °C. | Wt. % Adsorbed |
|---|---|---|---|---|
| $O_2$ | 3.46 | 100 | −183 | 10.7 |
| Neopentane | 6.2 | 700 | 23 | 1.1 |
| n-Hexane | 4.3 | 45 | 22 | 3.7 |
| n-Butane | 4.3 | 700 | 22 | 3.8 |
| iso-Butane | 5.0 | 700 | 22 | 0.0 |
| $H_2O$ | 2.65 | 4.6 | 22 | 12.4 |

From the above data, the pore size of the calcined product was determined to be greater than about 4.3 Å, as shown by the adsorption of n-hexane and n-butane (kinetic diameter of 4.3 Å), but less than about 5.0Å, as shown by the negligable adsorption of iso-butane (kinetic diameter of 5.0 Å).

EXAMPLE 6

(Preparation of GeAPO-31)

(a) GeAPO-31 is prepared from a reaction mixture having a composition, expressed in terms of the molar oxide ratios of the components of the reaction mixture of:

1.0–2.0 DPA:0.1–0.4 $GeO_2$:0.5–1.0 $Al_2O_3$:0.5–1.0 $P_2O_5$:40–100 $H_2O$ wherein "DPA" denotes di-n-propylamine.

The reaction mixture is seeded with crystals of AlPO$_4$-31 (U.S. Pat. No. 4,310,440) and digested by placing the reaction mixture in a sealed stainless steel pressure vessel and heating it at an effective temperature and for an effective time until crystals of the GeAPO-31 product ar obtained. Solids are then recovered by filtration, washed with water and dried in air at room temperature.

The GeAPO-31 product's chemical analysis shows GeAPO-31 contains germanium, aluminum and phosphorus in amounts within the pentagonal compositional area defined by points A, B, C, D and E of FIG. 1.

The X-ray powder diffraction pattern of a GeAPO-31 product is characterized by the following data:

| $2\theta$ | d (Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |

| 2θ | d (Å) | Relative Intensity |
|---|---|---|
| 31.7–31.8 | 2.823–2.814 | w–m |

(b) The X-ray powder diffraction pattern for a calcined GeAPO-31 is also characterized by the X-ray pattern of part (a).

(c) When the calcined GeAPO-31 of part (b) is utilized in adsorption capacity studies using a standard McBain-Bakr gravimetric adsorption apparatus the measurements are made on a sample after activation at 350° C. in vacuum. The following data are used in the adsorption studies:

| Adsorbate | Kinetic Diameter (Å) | Pressure (Torr) | Temp. °C. | Wt. % Adsorbed* |
|---|---|---|---|---|
| O₂ | 3.46 | 100 | −183 | 4 |
| O₂ | 3.46 | 750 | −183 | 6 |
| Cyclohexane | 6.0 | 90 | 24 | 3 |
| Neopentane | 6.2 | 700 | 24 | 3 |
| H₂O | 2.65 | 4.3 | 24 | 3 |
| H₂O | 2.65 | 20 | 24 | 10 |

*typical amount adsorbed

The pore diameter of GeAPO-31 is greater than about 6.2 Å.

EXAMPLE 7

(Preparation of GeAPO-34)

(a) GeAPO-34 is prepared from a reaction mixture having a composition, expressed in terms of the molar oxide ratios of the components of the reaction mixture of:

1.0–2.0 TEAOH:0.1–0.4 GeO₂:0.5–1.0 Al₂O₃:0.5–1.0 P₂O₅:40–100 H₂O where "TEAOH" denotes tetraethylammonium hydroxide.

The reaction mixture is digested by placing the reaction mixture in a sealed stainless steel pressure vessel and heating it at an effective temperature and for an effective time until crystals of the GeAPO-34 product are obtained. The solids are recovered by filtration, washed with water and dried in air at room temperature.

The GeAPO-34 product's chemical analysis shows GeAPO-31 contains germanium, aluminum and phosphorus in amounts within the pentagonal compositional area defined by points A, B, C, D and E of FIG. 1.

The X-ray powder diffraction pattern of a GeAPO-34 product is characterized by the following data:

| 2θ | d (Å) | Relative Intensity |
|---|---|---|
| 9.4–9.65 | 9.41–9.17 | s–vs |
| 15.9–16.2 | 5.57–5.47 | vw–m |
| 17.85–18.4 | 4.97–4.82 | w–vs |
| 20.3–20.9 | 4.37–4.25 | m–vs |
| 24.95–25.4 | 3.57–3.51 | vs–s |
| 30.3–30.8 | 2.95–2.90 | w–s |

(b) The X-ray powder diffraction pattern for a calcined GeAPO-34 is also characterized by the X-ray pattern of part (a).

(c) When the calcined GeAPO-34 of part (b) is utilized in adsorption capacity studies using a standard McBain-Bakr gravimetric adsorption apparatus the measurements are made on a sample after activation at 350° C. in vacuum. The following data are used in the adsorption studies:

| Adsorbate | Kinetic Diameter (Å) | Pressure (Torr) | Temp. °C. | Wt. % Adsorbed* |
|---|---|---|---|---|
| O₂ | 3.46 | 100 | −183 | 13 |
| O₂ | 3.46 | 750 | −183 | 18 |
| n-Hexane | 4.3 | 100 | 24 | 6 |
| H₂O | 2.65 | 4.3 | 24 | 15 |
| H₂O | 2.65 | 20 | 24 | 21 |

*typical amount adsorbed.

The pore diameter of GeAPO-34 is about 4.3 Å.

EXAMPLE 8

(Preparation of GeAPO-44)

(a) GeAPO-44 is prepared from a reaction mixture having a composition, expressed in terms of the molar oxide ratios of the components of the reaction mixture of:

1.0–2.0 CHA:0.1–0.4 GeO₂:0.5–1.0 Al₂O₃:0.5–1.0 P₂O₅:40–100 H₂O where "CHA" denotes cyclohexylamine.

The reaction mixture is digested by placing the reaction mixture in a sealed stainless steel pressure vessel and heating it at an effective temperature and for an effective time until crystals of the GeAPO-44 product are obtained. The solids are recovered by filtration, washed with water and dried in air at room temperature.

The GeAPO-44 product's chemical analysis shows GeAPO-31 contains germanium, aluminum and phosphorus in amounts within the pentagonal compositional area defined by points A, B, C, D and E of FIG. 1.

The X-ray powder diffraction pattern of a GeAPO-44 product is characterized by the following data:

| 2θ | d (Å) | Relative Intensity |
|---|---|---|
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

(b) When the calcined GeAPO-44 is utilized in adsorption capacity studies using a standard McBain-Bakr gravimetric adsorption apparatus the measurements are made on a sample after activation at 350° C. in vacuum. The following data are used in the adsorption studies:

| Adsorbate | Kinetic Diameter (Å) | Pressure (Torr) | Temp. °C. | Wt. % Adsorbed* |
|---|---|---|---|---|
| O₂ | 3.46 | 100 | −183 | 13 |
| O₂ | 3.46 | 750 | −183 | 16 |
| n-Hexane | 4.3 | 100 | 24 | 2 |
| H₂O | 2.65 | 4.3 | 24 | 15 |
| H₂O | 2.65 | 20 | 24 | 7 |

*typical amount adsorbed.

The pore diameter of GeAPO-44 is about 4.3 Å.

EXAMPLE 9

(Preparation of GeAPO-18)

(a) To prepare GeAPO-18, a reaction mixture was formed by adding 30.0 grams of water to 40.9 grams of aluminum isopropoxide (Al(OC$_3$H$_7$)$_3$), and then adding 7.58 grams of germanium ethoxide (Ge(OC$_2$H$_5$)$_4$) The resultant mixture was blended with a Brookfield high speed mixer until homogeneous and dried at 100° C. overnight. To the resultant dry mixture was added a solution formed by mixing 23.1 grams of 85 wt. percent orthophosphoric acid (H$_3$PO$_4$), 19.8 grams of water and 73.5 grams of 40 wt. percent aqueous tetraethylammonium hydroxide (TEAOH) and the resultant mixture was stirred until homogeneous. The composition of the final reaction mixture thus produced, expressed in terms of the molar oxide ratios of the components of the reaction mixture, was:

2.0 TEAOH:0.3 GeO$_2$:1.0 Al$_2$O$_3$:1.0 P$_2$O$_5$:20 H$_2$O

This final reaction mixture was digested by sealing it in a stainless steel pressure vessel lined with polytetrafluoroethylene and heating it in an oven at 200° C. under autogenous pressure for 96 hours. The solid reaction product (which was determined by the analyses described below to be GeAPO-18) was recovered by centrifugation, washed with water and dried in air at ambient temperature, and then at 100° C. overnight.

A sample of this solid reaction product was analyzed and the following chemical analysis obtained:

| Component | Weight Percent |
|---|---|
| Carbon | 9.5 |
| Nitrogen | 1.4 |
| GeO$_2$ | 8.5 |
| Al$_2$O$_3$ | 33.3 |
| P$_2$O$_5$ | 38.3 |
| LOI* | 19.8 |

*LOI indicates loss on ignition.

The above chemical analysis corresponds to a product composition, on an anhydrous basis, in molar oxide ratios of:

0.30 TEAOH:0.25 GeO$_2$:1.0 Al$_2$O$_3$:0.83 P$_2$O$_5$ or an empirical formula of:

0.08 TEAOH:(Ge$_{0.06}$Al$_{0.51}$P$_{0.42}$)O$_2$ so that the product contained germanium, aluminum and phosphorus in amounts within the pentagonal compositional area defined by points A, B, C, D and E of FIG. 1.

The X-ray powder diffraction pattern of the product, as synthesized, was characterized by the data in the following Table FA:

TABLE FA (GeAPO-18)

| 2θ | d (Å) | Relative Intensity 100 × I/I$_o$ |
|---|---|---|
| 9.6 | 9.20 | 100.0 |
| 10.5 | 8.45 | 5.6 |
| 11.0 | 8.02 | 9.6 |
| 13.2 | 6.73 | 3.6 |
| 14.0 | 6.32 | 4.4 |
| 14.8 | 5.98 | 6.2 |
| 15.6 | 5.70 | 23.1 |
| 17.0 | 5.21 | 49.8 |
| 17.9 | 4.95 | 24.6 |
| 19.6 | 4.54 | 4.5 |
| 20.2 | 4.40 | 30.6 |
| 21.0 | 4.23 | 38.6 |
| 22.2 | 4.01 | 11.8 |
| 23.4 | 3.80 | 5.9 |
| 23.9 | 3.72 | 4.7 |
| 24.4 | 3.64 | 9.2 |
| 25.0 | 3.57 | 8.2 |
| 25.5 | 3.49 | 7.5 |
| 26.2 | 3.41 | 9.4 |
| 26.5 | 3.36 | 5.1 |
| 26.9 | 3.32 | 10.2 |
| 28.1 | 3.17 | 16.0 |
| 30.1 | 2.97 | 15.9 |
| 30.9 | 2.90 | 8.2 |
| 31.4 | 2.85 | 11.5 |
| 32.5 | 2.76 | 21.8 |

Other specimens of GeAPO-18 prepared in a similar manner had substantially the same X-ray powder diffraction pattern. The following general Table FB summarizes the X-ray powder diffraction lines which were obtained from the various specimens of GeAPO-18. The least intense lines were not obtained from every specimen.

TABLE FB (GeAPO-18)

| 2θ | d (Å) | Relative Intensity 100 × I/I$_o$ |
|---|---|---|
| 9.6–9.7 | 9.12–9.20 | 100.0 |
| 10.4–10.5 | 8.43–8.48 | 2.4–5.6 |
| 11.0 | 7.99–8.03 | 3.6–9.6 |
| 13.1–13.2 | 6.72–6.74 | 1.4–3.6 |
| 14.0–14.1 | 6.30–6.32 | 2.3–4.4 |
| 14.8–14.9 | 5.96–5.98 | 2.9–6.2 |
| 15.5–15.6 | 5.68–5.70 | 12.4–23.1 |
| 17.0–17.1 | 5.20–5.21 | 31.3–49.8 |
| 17.9–18.0 | 4.90–4.95 | 22.0–31.8 |
| 19.5–19.6 | 4.53–4.54 | 1.8–4.5 |
| 20.2 | 4.39–4.40 | 18.7–30.6 |
| 21.0 | 4.21–4.23 | 24.9–38.6 |
| 22.2 | 4.01 | 6.1–11.8 |
| 23.4 | 3.80–3.81 | 2.8–5.9 |
| 23.9–24.0 | 3.71–3.72 | 2.4–4.7 |
| 24.4–24.5 | 3.64 | 4.7–9.2 |
| 25.0 | 3.56–3.57 | 4.6–8.2 |
| 25.5–25.6 | 3.48–3.49 | 7.5–10.0 |
| 26.1–26.2 | 3.41 | 5.3–9.4 |
| 26.4–26.6 | 3.35–3.37 | 2.9–5.2 |
| 26.8–26.9 | 3.32 | 5.9–10.2 |
| 28.2–28.1 | 3.17–3.18 | 14.9–18.8 |
| 30.2–30.1 | 2.96–2.97 | 12.6–15.9 |
| 30.9 | 2.89–2.90 | 4.0–8.2 |
| 31.5–31.4 | 2.84–2.85 | 12.4–16.4 |
| 32.6–32.5 | 2.75–2.76 | 19.5–24.6 |

(b) A sample of the product produced in part (a) was utilized in adsorption capacity studies using a standard McBain-Bakr gravimetric adsorption apparatus. Before being used in the adsorption tests, the sample was calcined in air at 600° C. for 3 hours. The calcined sample was activated by heating to 350° C. for 16 hours in vacuum, and this activation was repeated before each new adsorbate. The following data were generated in the adsorption studies.

| Adsorbate | Kinetic Diameter (Å) | Pressure (Torr) | Temp. °C. | Wt. % Adsorbed |
|---|---|---|---|---|
| O$_2$ | 3.46 | 100 | −183 | 22.1 |
| Neopentane | 6.2 | 700 | 23 | 3.1 |

| Adsorbate | Kinetic Diameter (Å) | Pressure (Torr) | Temp. °C. | Wt. % Adsorbed |
|---|---|---|---|---|
| n-Hexane | 4.3 | 45 | 22 | 9.8 |
| n-Butane | 4.3 | 700 | 22 | 8.5 |
| iso-Butane | 5.0 | 700 | 22 | 1.4 |
| $H_2O$ | 2.65 | 4.6 | 22 | 28.1 |

From the above data, the pore size of the calcined product was determined to be greater than about 4.3 Å, as shown by the adsorption of n-hexane and n-butane (kinetic diameters of 4.3 Å), but less than about 5.0 Å, as shown by the negligible adsorption of iso-butane (kinetic diameter of 5.0 Å).

EXAMPLE 10

(Preparation of GeAPO-20)

(a) To prepare GeAPO-20, a reaction mixture was formed by mixing 40.9 grams of aluminum isopropoxide (Al(OC$_3$H$_7$)3) with 20.0 grams of water, then adding 7.58 grams of germanium ethoxide (Ge(OC$_2$H$_5$)$_4$) To the resultant mixture was added a solution of 23.1 grams of 85 wt. percent orthophosphoric acid (H$_3$PO$_4$) mixed with 19.2 grams of water, and the resultant mixture was blended with a solution prepared by dissolving 36.2 grams of tetramethylammonium hydroxide pentahydrate (TMAOH.5H$_2$O) in 23.9 grams of water. The final reaction mixture was then blended until homogeneous. The composition of the final reaction mixture thus produced, expressed in terms of the molar oxide ratios of the components of the reaction mixture, was:

2.0 TMAOH:0.3 GeO$_2$:1.0 Al$_2$O$_3$:1.0 P$_2$O$_5$:50.0 H$_2$O:1.2 C$_2$H$_5$OH:6.0 C$_3$H$_7$H

This final reaction mixture was digested by sealing it in a stainless steel pressure vessel lined with polytetrafluoroethylene and heating it in an oven at 200° C. under autogenous pressure for 96 hours. The solid reaction product (which was determined by the analyses described below to be GeAPO-20) was recovered by centrifugation, washed with water and dried in air at ambient temperature, and then in an oven at 100° C. A sample of this solid reaction product was analyzed and the following chemical analysis obtained:

| Component | Weight Percent |
|---|---|
| Carbon | 8.9 |
| Nitrogen | 2.0 |
| GeO$_2$ | 5.0 |
| Al$_2$O$_3$ | 34.5 |
| P$_2$O$_5$ | 42.4 |
| LOI* | 18.8 |

*LOI indicates loss on ignition.

The above chemical analysis corresponds to a product composition, on an anhydrous basis, in molar oxide ratios of:

0.55 TMAOH:0.14 GeO$_2$:1.0 Al$_2$O$_3$:0.88 P$_2$O$_5$ or an empirical formula of:

0.14 TMAOH:(Ge$_{0.04}$Al$_{0.51}$P$_{0.45}$)O$_2$ so that the product contained germanium, aluminum and phosphorus in amounts within the pentagonal compositional area defined by points A, B, C, D and E of FIG. 1.

Scanning electron microscopy of the solid reaction product showed numerous crystals having the morphology expected for GeAPO-20. Microprobe analysis of a clean crystal having this morphology indicated the following composition:

Ge$_{0.07}$Al$_{0.48}$P$_{0.45}$ thus again indicating that the product contained germanium, aluminum and phosphorus in amounts within the pentagonal composition area defined by points A, B, C, D and E of FIG. 1.

The X-ray powder diffraction pattern of the product, as synthesized, was characterized by the data in the following Table GA:

TABLE GA (GeAPO-20)

| 2θ | d (Å) | Relative Intensity 100 × I/I$_o$ |
|---|---|---|
| 13.9 | 6.37 | 47.3 |
| 19.8 | 4.49 | 44.7 |
| 22.1 | 4.02 | 8.7 |
| 24.3 | 3.67 | 100.0 |
| 28.1 | 3.17 | 13.6 |
| 31.5 | 2.84 | 12.0 |
| 34.6 | 2.59 | 16.2 |
| 40.2 | 2.24 | 3.9 |
| 42.8 | 2.12 | 4.6 |
| 47.5 | 1.91 | 4.2 |
| 52.0 | 1.76 | 8.1 |

(b) A sample of the product produced in part (a) was utilized in adsorption cppacity studies using a standard McBain-Bakr gravimetric adsorption apparatus. Before being used in the adsorption tests, the sample was calcined in air at 600° C. for 3 hours. The calcined sample was activated by heating to 350° C. for 16 hours in vacuum, and this activation was repeated before each new adsorbate. The following data were generated in the adsorption studies.

| Adsorbate | Kinetic Diameter (Å) | Pressure (Torr) | Temp. °C. | Wt. % Adsorbed |
|---|---|---|---|---|
| O$_2$ | 3.46 | 100 | −183 | 0.68 |
| Neopentane | 6.2 | 700 | 23 | 1.11 |
| n-Hexane | 4.3 | 45 | 22 | 0.82 |
| n-Butane | 4.3 | 700 | 22 | 0.58 |
| iso-Butane | 5.0 | 700 | 22 | 0.38 |
| H$_2$O | 2.65 | 4.6 | 22 | 16.83 |

From the above data, the pore size of the calcined product was determined to be greater than 2.65 Å, as shown by the adsorption of water (kinetic diameter of 2.65 Å), but less than about 3.46 Å, as shown by the negligible adsorption of oxygen (kinetic diameter of 3.46 Å).

EXAMPLE 11

(Preparation of GeAPO-20)

(a) To prepare GeAPO-20, a solution was formed by mixing 23.1 grams of 85 wt. percent orthophosphoric acid (H$_3$PO$_4$) mixed with 19.2 grams of water. To the resultant solution was added a slurry formed from 40.9 grams of aluminum isopropoxide (Al(OC$_3$H$_7$)3) and 20.0 grams of water. To the resultant mixture was added a solution containing 36.2 grams of tetramethylammonium hydroxide pentahydrate (TMAOH.5H$_2$O) and 3.14 grams of GeO$_2$ in 20.0 grams of water. The resultant mixture was blended thoroughly with a Brookfield high speed mixture until the final homogeneous reaction mixture was produced. The composition of the final reaction mixture thus produced, expressed in terms of the molar oxide ratios of the components of the reaction mixture, was:

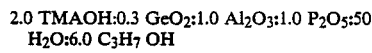
2.0 TMAOH:0.3 GeO$_2$:1.0 Al$_2$O$_3$:1.0 P$_2$O$_5$:50 H$_2$O:6.0 C$_3$H$_7$OH This final reaction mixture was digested by sealing it in a stainless steel pressure vessel lined with polytetrafluoroethylene and heating it in an oven at 200° C. under autogenous pressure for 192 hours. The solid reaction product (which was determined by the analyses described below to be GeAPO-20) was recovered by centrifugation, washed thoroughly with water and dried in air at ambient temperature, and then at 100° C. overnight. A sample of this solid reaction product was analyzed and the following chemical analysis obtained:

| Component | Weight Percent |
|---|---|
| Carbon | 8.9 |
| Nitrogen | 2.3 |
| GeO$_2$ | 6.3 |
| Al$_2$O$_3$ | 33.1 |
| P$_2$O$_5$ | 42.6 |
| LOI* | 17.1 |

*LOI indicates loss on ignition.

The above chemical analysis corresponds to a product composition, on an anhydrous basis, in molar oxide ratios of:

0.57 TMAOH:0.18 GeO$_2$:1.0 Al$_2$O$_3$:0.92 P$_2$O$_5$ or an empirical formula of:

0.14 TMAOH (Ge$_{0.05}$Al$_{0.05}$Al$_{0.50}$P$_{0.46}$)O$_2$ so that the product contained germanium, aluminum and phosphorus in amounts within the pentagonal compositional area defined by points A, B, C, D and E of FIG. 1.

Scanning electron microscopy of the product showed numerous crystals having the morphology expected for GeAPO-20. Microprobe analyses of clean crystals having this morphology indicated the following average composition:

Ge$_{0.05}$Al$_{0.45}$P$_{0.50}$ again confirming that the product contained germanium, aluminum and phosphorus in amounts within the pentagonal compositional area defined by points A, B, C, D and E of FIG. 1.

The X-ray powder diffraction pattern of the product, as synthesized, was similar to that of the GeAPO-20 produced in Example 10 above.

EXAMPLE 12

(Preparation of GeAPO-20)

To prepare GeAPO-20, a solution was formed by mixing 23.1 grams of 85 wt. percent orthophosphoric acid (H$_3$PO$_4$) with 14.2 grams of water. To this solution were added 13.6 grams of hydrated aluminum oxide in the form of a pseudo-boehmite phase comprising 75.1 wt. percent of Al$_2$O$_3$ and 24.9 wt. percent of H$_2$O. To the resultant mixture was added a solution containing 36.2 grams of tetramethylammonium hydroxide pentahydrate (TMAOH.5H$_2$O) and 3.14 grams of germanium dioxide (GeO$_2$) in 20 grams of water. The resultant mixture was blended thoroughly with a Brookfield high speed mixer until homogeneous to produce the final reaction mixture. The composition of the final reaction mixture thus produced, expressed in terms of the molar oxide ratios of the components of the reaction mixture, was:

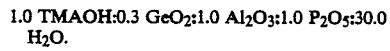
1.0 TMAOH:0.3 GeO$_2$:1.0 Al$_2$O$_3$:1.0 P$_2$O$_5$:30.0 H$_2$O.

This final reaction mixture was digested by sealing it in a stainless steel pressure vessel lined with polytetrafluoroethylene and heating it in an oven at 200° C. under autogenous pressure for 24 hours. The solid reaction product (which was determined by the analyses described below to be a mixture containing GeAPO-20) was recovered by centrifugation, washed thoroughly with water and dried in air at ambient temperature, and then at 100° C. overnight. A sample of this solid reaction product was analyzed and the following chemical analysis obtained:

| Component | Weight Percent |
|---|---|
| Carbon | 9.8 |
| Nitrogen | 2.7 |
| GeO$_2$ | 9.5 |
| Al$_2$O$_3$ | 32.3 |
| P$_2$O$_5$ | 38.8 |
| LOI* | 17.7 |

*LOI indicates loss on ignition.

The above chemical analysis corresponds to a product composition, on an anhydrous basis, in molar oxide ratios of:

0.64 TMAOH:0.29 GeO$_2$:1.0 Al$_2$O$_3$:0.86 P$_2$O$_5$ or an empirical formula, on an anhydrous basis, of:

0.16 TMAOH:(Ge$_{0.07}$Al$_{0.50}$P$_{0.43}$)O$_2$ so that the product contained germanium, aluminum and phosphorus in amounts within the pentagonal compositional area defined by points A, B, C, D and E of FIG. 1.

Scanning electron microscopy of the solid reaction product showed numerous crystals with the morphology expected for GeAPO-20. Microprobe analysis of a clean crystal having this morphology indicated the following composition:

Ge$_{0.11}$Al$_{0.50}$P$_{0.39}$ again indicating that the product contained germanium aluminum and phosphorus in amounts within the pentagonal compositional area defined by points A, B, C, D and E of FIG. 1.

The X-ray powder diffraction pattern of the product, as synthesized, was similar to that of the GeAPO-20 produced in Example 10 above.

All the specimens of GeAPO-20 produced in Examples 10, 11 and 12 above had similar X-ray powder diffraction patterns. The following general Table GB summarizes the X-ray powder diffraction lines which were obtained from the various specimens of GeAPO-20. The least intense lines were not obtained from every specimen.

TABLE GB (GeAPO-20)

| 2θ | d (Å) | Relative Intensity 100 × I/I$_o$ |
|---|---|---|
| 14.0–13.9 | 6.34–6.37 | 42.5–48.5 |
| 19.7–19.8 | 4.49–4.51 | 42.1–44.7 |
| 22.0–22.2 | 4.01–4.04 | 8.2–10.0 |
| 24.2–24.3 | 3.66–3.69 | 100.0 |
| 28.0–28.2 | 3.17–3.19 | 11.0–14.0 |
| 31.4–31.6 | 2.84–2.86 | 11.8–12.4 |
| 34.4–34.7 | 2.59–2.60 | 16.8–17.4 |
| 40.0–40.2 | 2.24–2.26 | 3.9–4.6 |
| 42.5–42.8 | 2.12–2.13 | 2.8–4.6 |
| 47.2–47.6 | 1.91–1.92 | 4.2–5.1 |
| 51.7–52.0 | 1.76–1.77 | 8.1–9.4 |

EXAMPLE 13

(Preparation of GeAPO-33)

As indicated above, the product produced in Example 12 was impure. In addition to the X-ray powder diffraction pattern of GeAPO-20 given in Table GA above, the solid reaction product showed a further X-ray powder diffraction pattern due to a further major phase characterized by the data in the following Table JA. This major phase was identified from its X-ray powder diffraction pattern given in Table JA below as GeAPO-33.

TABLE JA (GeAPO-33)

| 2θ | d (Å) | Relative Intensity |
|---|---|---|
| 9.3 | 9.47 | 6.0 |
| 12.6 | 7.00 | 31.0 |
| 14.5 | 6.12 | 1.7 |
| 15.3 | 5.79 | 4.1 |
| 23.0 | 3.87 | 2.3 |
| 26.1 | 3.41 | 8.2 |
| 27.4 | 3.26 | 33.9 |
| 29.5 | 3.02 | 3.5 |
| 32.1 | 2.79 | 2.6 |
| 40.0 | 2.25 | 5.2 |
| 47.9 | 1.90 | 2.1 |

Scanning electron microscopy of the solid reaction product referred to above showed crystals having the morphology expected for GeAPO-33. Microprobe analysis of a clean crystal having this morphology indicated the following composition:

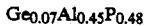

Ge$_{0.07}$Al$_{0.45}$P$_{0.48}$ so that the GeAPO-33 product contained germanium, aluminum and phosphorus in amounts within the hexagonal compositional area defined by points A, B, C, D and E of FIG. 1.

PROCESS APPLICATIONS

The GeAPO compositions of the present invention are, in general, hydrophilic and adsorb water preferentially over common hydrocarbon molecules such as paraffins, olefins and aromatic species, e.g., benzene, xylenes and cumene. Thus the present molecular sieve compositions as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These GeAPOs are therefore suitably employed in the drying of reformer hydrogen streams and in the drying of oxygen, nitrogen or air prior to liquifaction.

The present GeAPO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art (e.g. ion exchange) and used, for example, in fabricating catalyst compositions having silica or alumina bases. The pore diameters of the GeAPO compositions range from less than 3.46Å to greater than 6.2Å; those species having pores larger than about 4Å are preferred for catalytic applications.

Among the hydrocarbon conversion reactions catalyzed by GeAPO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using GeAPO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. (204° C. to 441° C.) using molar ratios of hydrogen to hydrocarbon in the range of between 2 and 80, pressures between 10 and 3500 p.s.i.g. (0.171 to 24.23 MPa.), and a liquid hourly space velocity (LHSV) of from 0.1 to 20, preferably 1.0 to 10.

The GeAPO catalyst compositions employed in hydrocracking are also suitable for use in reforming processes in which the hydrocarbon feedstocks contact the catalyst at temperatures of from about 700° F. to 1000° F. (371° C. to 538° C.), hydrogen pressures of from 100 to 500 p.s.i.g. (0.791 to 3.448 MPa.), LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerization processes in which feedstocks such as normal paraffins are converted to saturated branched chain isomers. Hydroisomerization is carried out at a temperature of from about 200° F. to 600° F. (93° C. to preferably 300° F. to 550° F. (149° C. to 288° C.) with 316° C.), preferably 300° F. to 550° F. (149° C. to 288° C.) with an LHSV value of from about 0.2 to 1.0. Hydrogen (H) is supplied to the reactor in admixture with the hydrocarbon (Hc) feedstock in molar proportions (H/Hc) of between 1 and 5.

At somewhat higher temperatures, i.e. from about 650° F. to 1000° F. (343° C. to 538° C.), preferably 850° F. to 950° F. (454° C. to 510° C.) and usually at somewhat lower pressures within the range of about 15 to 50 p.s.i.g. (205 to 446 KPa.), the same catalyst compositions are used to hydroisomerize normal paraffins. Preferably the paraffin feedstock comprises normal paraffins having a carbon number range of C$_7$–C$_{20}$. Contact time between the feedstock and the catalyst is generally relatively short to avoid undesirable side reactions such as olefin polymerization and paraffin cracking. LHSV values in the range of 0.1 to 10, preferably 1.0 to 6.0 are suitable.

The unique crystal structure of the present GeAPO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F. (204° to 399° C.), pressures in the range of 100 to 2000 p.s.i.g. (0.791 to 13.89 MPa.) and LHSV values in the range of 0.1 to 15.

Catalytic cracking processes are preferably carried out with GeAPO compositions using feedstocks such as gas oils, heavy naphthas, deasphalted crude oil residua, etc., with gasoline being the principal desired product. Temperature conditions of 850° to 1100° F. (454° to 593° C.), C), LHSV values of 0.5 to 10 and pressure conditions of from about 0 to 50 p.s.i.g. (101 to 446 KPa.) are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the GeAPO catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°–1000° F. (427°–538° C.) are employed at moderate hydrogen pressures of about 300–1000 p.s.i.g. (2.17–6.895 MPa.), other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like. Any of these may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of hydrocracking catalysts. Consequently, it is necessary to operate at more extreme conditions when it is desired to obtain the same degree of hydrocracking conversion per pass on a relatively nitrogenous feed than with a feed containing less organonitrogen compounds. Consequently, the conditions under which denitrogenation, desulfurization and/or hydrocracking can be most expeditiously accomplished in any given situation are necessarily determined in view of the characteristics of the feedstocks, in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organo-nitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°–900° F. (260°–482° C.), while paraffins, naphthenes and alkyl aromatics are isomerized at temperatures of 700°–1000° F. (371°–538° C.). Particularly desirable isomerization contemplated herein include the conversion of n-heptene and/or n-octane to isoheptanes, iso-octanes, butane to iso-butane, methylcyclopentane to cyclohexane, meta-xylene and/or ortho-xylene to paraxylene, 1-butene to 2-butene and/or isobutene, n-hexane to isohexene, cyclohexene to methylcyclopentene etc. The preferred form of the catalyst is a combination of the GeAPO with polyvalent metal compounds (such as sulfides) of metals of Group II-A, Group II-B and rare earth metals. For alkylation and dealkylation processes the GeAPO compositions having pores of at least 5Å are preferred. When employed for dealkylation of alkyl aromatics, the temperature is usually at least 350° F. (177° C.) and ranges up to a temperature at which substantial cracking of the feedstock or conversion products occurs, generally up to about 700° F. (371° C.). The temperature is preferably at least 450° F. (232° C.) and not greater than the critical temperature of the compound undergoing dealkylation. Pressure conditions are applied to retain at least the aromatic feed in the liquid state. For alkylation the temperature can be as low as 250° F. (121° C.) but is preferably at least 350° F. (177° C.). In the alkylation of benzene, toluene and xylene, the preferred alkylating agents are olefins such as ethylene and propylene.

We claim:

1. A crystalline molecular sieve having a three-dimensional microporous framework structure of $GeO_2$, $AlO_2$ and $PO_2$ tetrahedral units having an empirical chemical composition of an anhydrous basis expressed by the formula:

$$mR:(Ge_xAl_yP_z)O_2$$

wherein "R" represents at least one organic templating agent present in the in-tracrystalline pore system; "m" represents the molar amount of "R" present per mole of $(Ge_xAl_yP_z)O_2$ and has a value of zero to about 0.3; and "x", "y" and "z" represent the mole fractions of germanium, aluminum and phosphorous, respectively, present as tetrahedral oxides, said fractions being such that they are within the pentagonal compositional area defined by points A, B, C, D and E of FIG. 1, said crystalline molecular sieves having a characteristic X-ray powder diffraction pattern which contains at least the d-spacings set forth in one of the following Tables C, F, J, N, P, U and V;

TABLE C

| 2θ | (GeAPO-14) d(Å) | Relative Intensity |
|---|---|---|
| 8.6–8.9 | 10.39–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE F

| 2θ | (GeAPO-18) d(Å) | Relative Intensity |
|---|---|---|
| 9.6–9.7 | 9.21–9.11 | vs |
| 15.5–15.6 | 5.72–5.70 | w–m |
| 16.9–17.1 | 5.25–5.19 | m |
| 20.15–20.25 | 4.41–4.39 | m |
| 20.95–21.05 | 4.24–4.22 | w–m |
| 31.8–32.6 | 2.814–2.75 | m |

TABLE J*

| 2θ | (GeAPO-33) d(Å) | Relative Intensity |
|---|---|---|
| 9.25–9.55 | 9.56–9.26 | w–m |
| 12.5–12.9 | 7.08–6.86 | vs |
| 15.3 | 5.79 | w |
| 26.05–26.35 | 3.42–3.38 | w–m |
| 27.3–27.6 | 3.27–3.23 | vs |
| 40.0 | 2.25 | w |

*as synthesized form

TABLE N

| 2θ | (GeAPO-36) d(Å) | Relative Intensity |
|---|---|---|
| 7.7–7.9 | 11.5–11.2 | vs |
| 16.2–16.6 | 5.47–5.34 | w–m |
| 18.9–19.3 | 4.70–4.60 | m–s |
| 20.6–20.8 | 4.31–4.27 | w–s |
| 21.8–22.0 | 4.08–4.04 | m |
| 22.2–22.5 | 4.00–3.95 | w–m |

TABLE P

| 2θ | (GeAPO-39) d(Å) | Relative Intensity |
|---|---|---|
| 9.4–9.6 | 9.41–9.21 | w–m |
| 13.3–13.6 | 6.66–6.51 | m–vs |
| 18.0–18.4 | 4.83–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE U

| 2θ | (GeAPO-46) d(Å) | Relative Intensity |
|---|---|---|
| 7.2–8.1 | 12.3–10.9 | vs |
| 21.2–21.8 | 4.19–4.08 | w–m |
| 22.5–23.0 | 3.95–3.8 | vw–m |
| 26.6–27.2 | 3.351–3.278 | vw–w |
| 28.5–29.0 | 3.132–3.079 | vw–w |

TABLE V

| 2θ | (GeAPO-47) d(Å) | Relative Intensity |
|---|---|---|
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w |

2. The crystalline molecular sieve of claim 1 where the mole fractions of germanium, aluminum and phosphorus present as tetrahedral oxides are within the pentagonal compositional area defined by points a, b, c, d and e of FIG. 2.

3. The crystalline molecular sieves of claim 1 or 2 having a characteristic x-ray powder diffraction pattern which contains at least the d-spacings set forth in Table C given in claim 1.

4. The crystalline molecular sieves of claim 1 or 2 having a characteristic X-ray powder diffraction pattern which contains at least the d-spacings set forth in Table F given in claim 1.

5. The crystalline molecular sieves of claim 4 wherein the X-ray powder diffraction pattern set forth in Table F contains at least the d-spacings set forth in the following Table FA;

TABLE FA

| 2θ | (GeAPO-18) d(Å) | Relative Intensity 100 × I/I₀ |
|---|---|---|
| 9.6 | 9.20 | 100.0 |
| 10.5 | 8.45 | 5.6 |
| 11.0 | 8.02 | 9.6 |
| 13.2 | 6.73 | 3.6 |
| 14.0 | 6.32 | 4.4 |
| 14.8 | 5.98 | 6.2 |
| 15.6 | 5.70 | 23.1 |
| 17.0 | 5.21 | 49.8 |
| 17.9 | 4.95 | 24.6 |
| 19.6 | 4.54 | 4.5 |
| 20.2 | 4.40 | 30.6 |
| 21.0 | 4.23 | 38.6 |
| 22.2 | 4.01 | 11.8 |
| 23.4 | 3.80 | 5.9 |
| 23.9 | 3.72 | 4.7 |
| 24.4 | 3.64 | 9.2 |
| 25.0 | 3.57 | 8.2 |
| 25.5 | 3.49 | 7.5 |
| 26.2 | 3.41 | 9.4 |
| 26.5 | 3.36 | 5.1 |
| 26.9 | 3.32 | 10.2 |
| 28.1 | 3.17 | 16.0 |
| 30.1 | 2.97 | 15.9 |
| 30.9 | 2.90 | 8.2 |
| 31.4 | 2.85 | 11.5 |
| 32.5 | 2.76 | 21.8. |

6. The crystalline molecular sieves of claim 1 or 2 having a characteristic X-ray powder diffraction pattern which contains at least the d-spacings set forth in Table J given in claim 1.

7. The crystalline molecular sieves of claim 6 wherein the X-ray powder diffraction pattern set forth in Table J contains at least the d-spacings set forth in the following Table JA;

TABLE JA

| 2Θ | (GeAPO-33) d(Å) | Relative Intensity 100 × I/I₀ |
|---|---|---|
| 9.3 | 9.47 | 6.0 |

TABLE JA-continued (GeAPO-33)

| 2Θ | d(Å) | Relative Intensity 100 × I/I$_o$ |
|---|---|---|
| 12.6 | 7.00 | 31.0 |
| 14.5 | 6.12 | 1.7 |
| 15.3 | 5.79 | 4.1 |
| 23.0 | 3.87 | 2.3 |
| 26.1 | 3.41 | 8.2 |
| 27.4 | 3.26 | 33.9 |
| 29.5 | 3.02 | 3.5 |
| 32.1 | 2.79 | 2.6 |
| 40.0 | 2.25 | 5.2 |
| 47.9 | 1.90 | 2.1 |

8. The crystalline molecular sieves of claim 1 or 2 having a characteristic X-ray powder diffraction pattern which contains at least the d-spacings set forth in Table N given in claim 1.

9. The crystalline molecular sieves of claim 1 or 2 having a characteristic X-ray powder diffraction pattern which contains at least the d-spacings set forth in Table P given in claim 1.

10. The crytstalline molecular sieves of claim 1 or 2 having a characterisic X-ray powder diffraction pattern which contains at least the d-spacings set forth in Table U given in claim 1.

11. The crystalline molecular sieves of claim 1 or 2 having a characteristic X-ray powder diffraction pattern which contains at least the d-spacings set forth in Table V given in claim 1.

12. Molecular sieve prepared by calcining at a temperature sufficienty hig to remove at least some of any organic templating agent present in the intracrystalline pore system, a crystalline molecular sieve having three-dimensional microporous framework structures of $GeO_2$, $AlO_2$ and $PO_2$ tetrahedral units having an empirical chemical composition on an anhydrous basis expressed by the formula:

$$mR:(Ge_xAl_yP_z)O_2$$

wherein "R" represents at least one organic templating agent present in the intracrystalline pore system; "m" represents the molar amount of "R" present per mole of $(Ge_xAl_yP_z)O_2$ and has a value of zero to about 0.3; and "x", "y" and "z" represent the mole fractions of germanium, aluminum and phosphorus, respectively, present as tetrahedral oxides, said mole fractions being such that they are within the pentagonal compostional area defined by points A, B, C, D and E of FIG. 1, said crystalline molecular sieves having a characteristic X-ray powder diffraction pattern which contains at least the d-spacings set forth in one of the following Tables C, F, J, N, U and V;

TABLE C (GeAPO-14)

| 2θ | d(Å) | Relative Intensity |
|---|---|---|
| 8.6–8.9 | 10.39–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE F (GeAPO-18)

| 2θ | d(Å) | Relative Intensity |
|---|---|---|
| 9.6–9.7 | 9.21–9.11 | vs |
| 15.5–15.6 | 5.72–5.70 | w–m |
| 16.9–17.1 | 5.25–5.19 | m |
| 20.15–20.25 | 4.41–4.39 | m |
| 20.95–21.05 | 4.24–4.22 | w–m |
| 31.8–32.6 | 2.814–2.75 | m |

TABLE J*

(GeAPO-33)

| 2θ | d(Å) | Relative Intensity |
|---|---|---|
| 9.25–9.55 | 9.56–9.26 | w–m |
| 12.5–12.9 | 7.08–6.86 | vs |
| 15.3 | 5.79 | w |
| 26.05–26.35 | 3.42–3.38 | w–m |
| 27.3–27.6 | 3.27–3.23 | vs |
| 40.0 | 2.25 | w |

*as synthesized form

TABLE N (GeAPO-36)

| 2θ | d(Å) | Relative Intensity |
|---|---|---|
| 7.7–7.9 | 11.5–11.2 | vs |
| 16.2–16.6 | 5.47–5.34 | w–m |
| 18.9–19.3 | 4.70–4.60 | m–s |
| 20.6–20.8 | 4.31–4.27 | w–s |
| 21.8–22.0 | 4.08–4.04 | m |
| 22.2–22.5 | 4.00–3.95 | w–m |

TABLE P (GeAPO-39)

| 2θ | d(Å) | Relative Intensity |
|---|---|---|
| 9.4–9.6 | 9.41–9.21 | w–m |
| 13.3–13.6 | 6.66–6.51 | m–vs |
| 18.0–18.4 | 4.83–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE U (GeAPO-46)

| 2θ | d(Å) | Relative Intensity |
|---|---|---|
| 7.2–8.1 | 12.3–10.9 | vs |
| 21.2–21.8 | 4.19–4.08 | w–m |
| 22.5–23.0 | 3.95–3.8 | vw–m |
| 26.6–27.2 | 3.351–3.278 | vw–w |
| 28.5–29.0 | 3.132–3.079 | vw–w |

TABLE V (GeAPO-47)

| 2θ | d(Å) | Relative Intensity |
|---|---|---|
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w |

13. Process for preparing crystalline molecular sieves having three-dimensional framework structures of $GeO_2$, $AlO_2$ and $PO_3$ tetrahedral units having an empirical chemical composition on an anhydrous basis expressed by the formula:

$mR:(Ge_xAl_yP_z)O_2$ wherein "r" represents at least one organic templating agent present in the intracrystalline pore system; "m" represents the molar amount of "r" present per mole of $(Ge_xAl_yP_z)O_2$ and has a value of zero to about 0.3; and "x", "y" and "z" represent the mole fractions of germanium, aluminum and phosphorus, respectively, present as tetrahedral oxides, said mole fractions being such that they are within the pentagonal compositional area defined by points A, B, C, D and E of FIG. 1, said crystalline molecular sieves having a characteristic X-ray powder diffraction pattern which contains at least the d-spacings set forth in one of the following Tables C, F, J, N, P, U and V;

TABLE C

| | (GeAPO-14) | |
|---|---|---|
| 2θ | d(Å) | Relative Intensity |
| 8.6–8.9 | 10.39–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE F

| | (GeAPO-18) | |
|---|---|---|
| 2θ | d(Å) | Relative Intensity |
| 9.6–9.7 | 9.21–9.11 | vs |
| 15.5–15.6 | 5.72–5.70 | w–m |
| 16.9–17.1 | 5.25–5.19 | m |
| 20.15–20.25 | 4.41–4.39 | m |
| 20.95–21.05 | 4.24–4.22 | w–m |
| 31.8–32.6 | 2.814–2.75 | m |

TABLE J*

| | (GeAPO-33) | |
|---|---|---|
| 2θ | d(Å) | Relative Intensity |
| 9.25–9.55 | 9.56–9.26 | w–m |
| 12.5–12.9 | 7.08–6.86 | vs |
| 15.3 | 5.79 | w |
| 26.05–26.35 | 3.42–3.38 | w–m |
| 27.3–27.6 | 3.27–3.23 | vs |
| 40.0 | 2.25 | w |

*as synthesized form

TABLE N

| | (GeAPO-36) | |
|---|---|---|
| 2θ | d(Å) | Relative Intensity |
| 7.7–7.9 | 11.5–11.2 | vs |
| 16.2–16.6 | 5.47–5.34 | w–m |
| 18.9–19.3 | 4.70–4.60 | m–s |
| 20.6–20.8 | 4.31–4.27 | w–s |
| 21.8–22.0 | 4.08–4.04 | m |
| 22.2–22.5 | 4.00–3.95 | w–m |

TABLE P

| | (GeAPO-39) | |
|---|---|---|
| 2θ | d(Å) | Relative Intensity |
| 9.4–9.6 | 9.41–9.21 | w–m |
| 13.3–13.6 | 6.66–6.51 | m–vs |
| 18.0–18.4 | 4.83–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE U

| | (GeAPO-46) | |
|---|---|---|
| 2θ | d(Å) | Relative Intensity |
| 7.2–8.1 | 12.3–10.9 | vs |
| 21.2–21.8 | 4.19–4.08 | w–m |
| 22.5–23.0 | 3.95–3.8 | vw–m |
| 26.6–27.2 | 3.351–3.278 | vw–w |
| 28.5–29.0 | 3.132–3.079 | vw–w |

TABLE V

| | (GeAPO-47) | |
|---|---|---|
| 2θ | d(Å) | Relative Intensity |
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w | the process comprising providing a reaction mixture composition to an effective temperature and for an effective time sufficient to produce said molecular sieves, said reaction mixture composition being expressed in terms of molar oxide ratios as follows $aR:(Ge_wAl_uP_x) O_2:bH_2O$ wherein "R" is an organic templating agent, "a" is an effective amount of "R" greater than zero; "b" has a value of from zero to about 500; and "w", "u" and "v" represent the mole fractions, respectively, of germanium, aluminum and phosphorus in the $(Ge_wAl_uP_v)O_2$ constituent, and each has a value of at least 0.01.

14. The process of claim 13 wherein "w", "y" and "z" are within the pentagonal compositional area defined by points F, G, H, I and J of FIG. 3.

15. The process of claim 13 wherein "a" is in the range of greater than zero to about 6.

16. The process of claim 13 wherein "a" is not greater than about 0.6.

17. The process of claim 13 wherein "b" is not greater than about 60.

18. Process according to claim 13 wherein the reaction mixture comprises from about 0.2 to about 0.4 moles of $GeO_2$ per mole of $P_2O_5$.

19. Process according to claim 13 wherein the reaction mixture comprises rom about 0.75 to about 1.25 moles of $Al_2O_3$ per mole of $P_2O_5$.

20. Process according to claim 13 wherein the source of phosphorus in the reaction mixture is orthophosphoric acid.

21. Process according to claim 20 wherein the source of phosphorus in the reaction mixture is orthophosphoric acid and the source of aluminum is at least one compound selected from the group consisting of pseudo-boehmite and aluminum alkoxide.

22. Process according to claim 21 wherein the aluminum alkoxide is aluminum isopropoxide or aluminum sec-butoxide.

23. Process according to claim 13 wherein the source of aluminum is aluminum chlorhydrol.

24. Process according to claim 13 wherein the source of germanium is selected from the group consisting of oxides, alkoxides, hydroxides, chlorides, bromides, iodides, nitrates, sulfates, carboxylates and mixtures thereof.

25. Process according to claim 24, wherein the source of germanium is selected from the group consisting of germanium dioxide, germanium ethoxide and germanium tetrachloride.

26. Process according to claim 13 or 14 wherein the organic templating agent is a quaternary ammonium or quaternary phosphonium compound having the formula:

$R_4X^+$ wherein X is nitrogen or phosphorus and each R is an alkyl or aryl group containing from 1 to 8 carbon atoms.

27. Process according to claim 13 wherein the organic templating agent is an amine.

28. Process according to claim 13 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-dimethylethanolamine; choline; N,N-dimethylpiperazine; 1,4-diaziabicyclo-(2,2,2) octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; tetramethylammonium ion; tetrabutylammonium ion; tetrapentylammonium ion; di-n-butylamine; neopentylamine; di-n-pentylamine; isopropylamine; t-butylamine; ethylenediamine; pyrroldine; 2-imidazolidone; di-n-propylamine; and a polymeric quaternary ammonium salt $[(C_{14}H_{32}N_2)(OH)_2]_x$ wherein x has a value of at least 2.

* * * * *